United States Patent
Cao et al.

(10) Patent No.: US 9,612,224 B2
(45) Date of Patent: Apr. 4, 2017

(54) HIGH DENSITY NANO-ARRAY FOR SENSING

(71) Applicant: INTERNATIONAL BUSINESS MACHINES CORPORATION, Armonk, NY (US)

(72) Inventors: Qing Cao, Yorktown Heights, NY (US); Kangguo Cheng, Schenectady, NY (US); Zhengwen Li, Scarsdale, NY (US); Fei Liu, Yorktown Heights, NY (US); Zhen Zhang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/725,067

(22) Filed: May 29, 2015

(65) Prior Publication Data

US 2016/0349207 A1 Dec. 1, 2016

(51) Int. Cl.
*G01N 27/414* (2006.01)

(52) U.S. Cl.
CPC .............................. *G01N 27/4146* (2013.01)

(58) Field of Classification Search
USPC ........................................................ 257/253
See application file for complete search history.

(56) References Cited

U.S. PATENT DOCUMENTS

| | | | |
|---|---|---|---|
| 8,052,931 B2 | 11/2011 | Bansal et al. | |
| 8,828,138 B2 | 9/2014 | Bedell et al. | |
| 8,987,841 B2 * | 3/2015 | Bikumandla | G01N 27/4148 204/403.01 |
| 2007/0096164 A1 * | 5/2007 | Peters | B82Y 15/00 257/253 |
| 2010/0055699 A1 | 3/2010 | Kahya | |
| 2010/0066348 A1 | 3/2010 | Merz et al. | |
| 2011/0033952 A1 | 2/2011 | Khater et al. | |
| 2013/0214332 A1 | 8/2013 | Wu | |
| 2013/0291627 A1 | 11/2013 | Hu et al. | |
| 2014/0308752 A1 | 10/2014 | Chang et al. | |

OTHER PUBLICATIONS

Ahn, J.H., et al., "CMOS-Based Biosensors with an Independent Double-Gate FinFET," IEEE International Electron Devices Meeting (IEDM), Dec. 2011. (pp. 1-4).

Buitrago, E., et al., "The top-down fabrication of a 3D-integrated, fully CMOS-compatibleFET biosensor based on vertically stacked SiNWs and FinFETs," Sensors and Actuators B: Chemical, vol. 193, Mar. 2014. (pp. 400-412).

* cited by examiner

*Primary Examiner* — Hrayr A Sayadian
(74) *Attorney, Agent, or Firm* — Tutunjian & Bitetto, P.C.; Vazken Alexanian

(57) ABSTRACT

A sensor includes a semiconductor substrate having first pointed nodes extending into a channel from a first side of the channel. Second pointed nodes extend into the channel from a second side of the channel, which is opposite the first side. The second pointed nodes being self-aligned to the first pointed nodes on the opposite side of the channel. The first pointed nodes and the second pointed nodes are connected to a circuit to detect particles in the channel.

7 Claims, 10 Drawing Sheets

HIGH DENSITY NANO-ARRAY FOR SENSING

BACKGROUND

Technical Field

The present invention relates to sensing devices and methods for fabricating sensing devices, and more particularly to a particle sensing device integrated into a semiconductor chip.

Description of the Related Art

Biosensors include many configurations and are employed for many applications. Some applications for biosensors include DNA sequencing, virus screening, cell isolation, etc. Conventional biosensors often include large dimensions and provide low precision/sensitivity.

SUMMARY

A sensor includes a semiconductor substrate having first pointed nodes extending into a channel from a first side of the channel. Second pointed nodes extend into the channel from a second side of the channel, which is opposite the first side. The second pointed nodes being self-aligned to the first pointed nodes on the opposite side of the channel. The first pointed nodes and the second pointed nodes are connected to a circuit to detect particles in the channel.

A method for forming a sensor includes forming a buried doping layer in a semiconductor substrate; forming fins in the substrate down to the buried doping layer; depositing a permeable filler material from the buried doping layer to a height along the fins; enclosing portions of the fin above the height in a non-permeable material; decomposing the fins within the filler material by permeating a reactant through the filler material to form first pointed nodes in the portions of the fins and second pointed nodes in the buried doping layer, the first and second pointed nodes being self-aligned to each other; and removing the filler material to form a channel for receiving materials to be sensed.

Another method for forming a sensor includes forming a buried doping layer in a semiconductor substrate; etching fins in the substrate down to the buried doping layer; depositing an oxygen permeable filler material from the buried doping layer to a height along the fins; enclosing portions of the fin above the height in a non-permeable nitride material; oxidizing the fins within the filler material to form self-aligned bird's peak points extending into the filler material from opposite sides; and removing the filler material to form a channel for receiving materials to be sensed.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Figure 2:
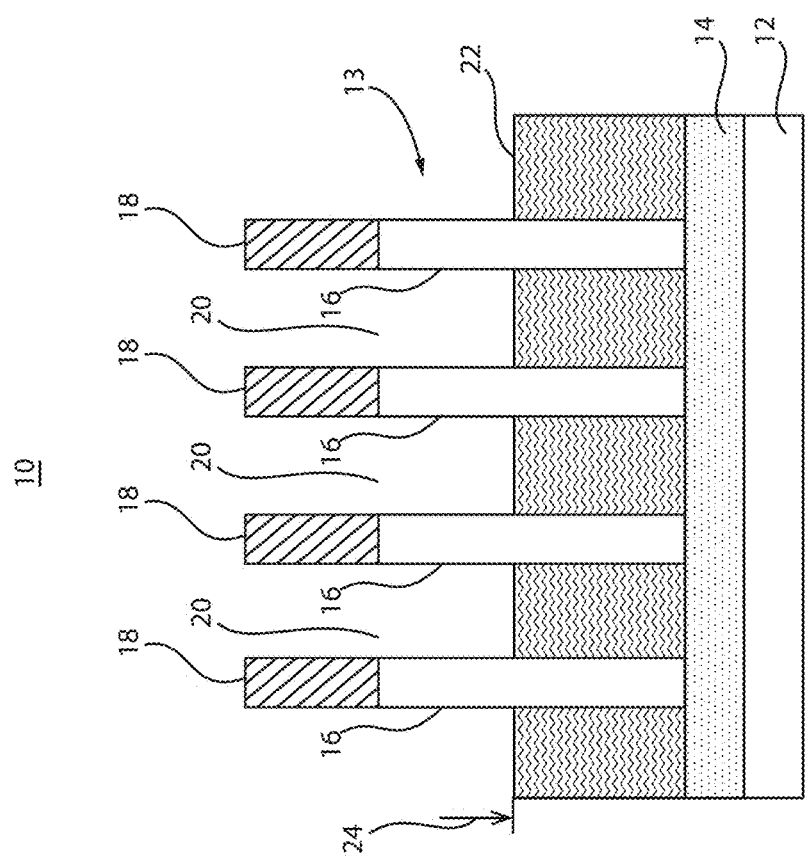
FIG. 2 is a cross-sectional view of a device of FIG. 1 showing fins etched into the substrate and a filler material filling regions between the fins in accordance with the present principles.

In accordance with the present principles, methods and structures are provided for forming vertical nanosensors with self-aligned electrodes. A fabrication process for the nanosensors is fully compatible with complementary metal oxide semiconductor (CMOS) processes so the nanosensor can be readily integrated with CMOS devices and structures. The methods provide pointed self-aligned electrodes on opposite sides of a fluidic channel. The structures can be configured for a plurality of applications including detecting organic or inorganic particles flowing through the channel or moving or filtering particles flowing through the channel. The present embodiments provide high density electrodes, e.g., 42 nm or less in pitch.

It is to be understood that the present invention will be described in terms of a given illustrative architecture or wafer structure; however, other architectures, structures, materials, process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

A design for an integrated circuit chip may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements may be included in the compound and still function in accordance with the present principles. The compounds with additional elements will be referred to herein as alloys.

The present embodiments may be part of a biosensor device or circuit, and the devices as described herein may be part of a design of an integrated circuit chip.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1:
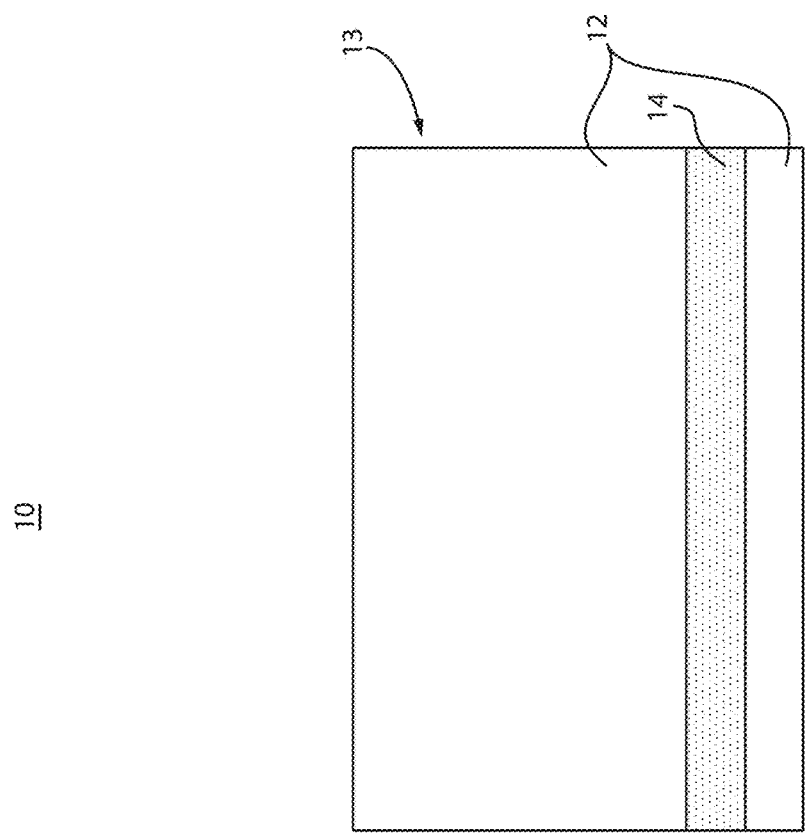
FIG. 1 is a cross-sectional view of a substrate having a buried layer formed therein in accordance with the present principles.

Referring now to the drawings in which like numerals represent the same or similar elements and initially to FIG. 1, illustrative embodiments are described for forming a biosensing device 10 in accordance with one exemplary embodiment. Device 10 begins with a substrate or substrate layer 12. The substrate 12 may include Si, SiGe, Ge, or any other substrate material(s). In one embodiment, Si is employed to be compatible with CMOS processing. A buried doping layer 14 is formed in the substrate 12 to provide a bottom electrode. The buried doping layer 14 may be formed by ion implantation of dopants. Alternatively, the buried doping layer 14 can be formed by in-situ doped epitaxial growth followed by undoped epitaxial growth to form a top layer 13 (the remaining portion of the substrate 12) over the buried doping layer 14.

Referring to FIG. 2, a portion 13 of the substrate 12 is etched to form fins 16. In one embodiment, the fins 16 may be formed using an etch mask. In one embodiment, to obtain a high density, a sidewall image transfer (SIT) process is employed. The SIT process includes forming mandrels (e.g., amorphous carbon mandrels, although other materials may be employed) on the substrate 12, forming sidewall spacers or caps 18 on sides of the mandrels. The spacers 18 may include nitride, e.g., silicon nitride, silicon oxinitride, etc. A dielectric (not shown) such as silicon oxide may be deposited on top of the substrate 12 before forming the mandrels. The mandrels are then removed and the spacers 18 are employed to etch the substrate 12 down to the doping layer 14 to form fins 16.

Gaps 20 between fins 16 are filled with a filler material 22. The filler material 22 may include an oxide, such as a silicon oxide. The filler material 22 includes a material permeable to oxygen or other agents that may be employed to decompose the fins 16 as will be described. The filler material 22 is then recessed to a height 24 using an etching process, e.g., a dry etch.

Figure 3:
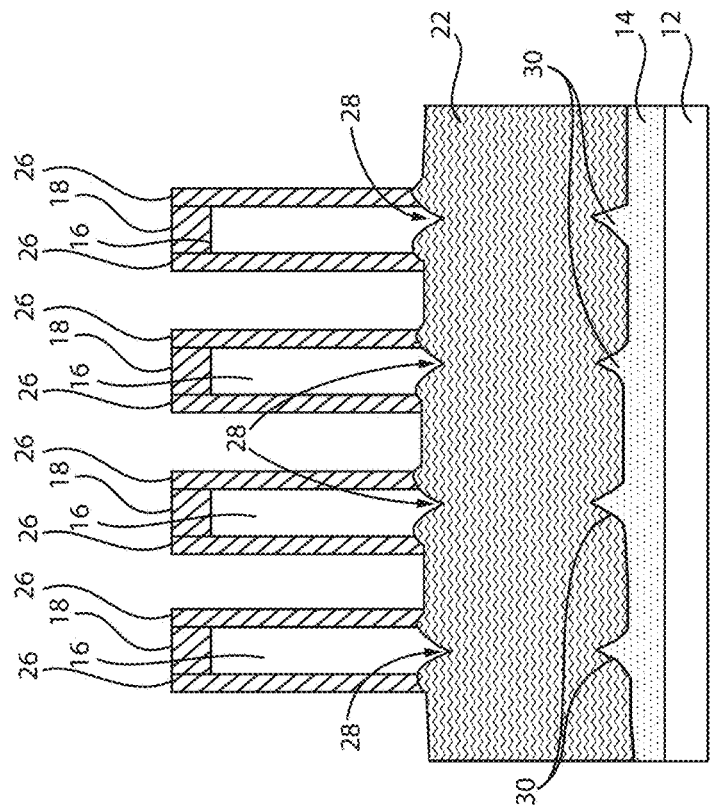
FIG. 3 is a cross-sectional view of the device of FIG. 2 showing portions of the fins enclosed within a non-permeable material in accordance with the present principles.

Referring to FIG. 3, sidewall spacers 26 are formed over the spacers 18 and exposed portions of the fins 16 over the filler material 22 (e.g., above height 24). The spacers 26 may include nitride, e.g., silicon nitride, silicon oxinitride, etc. The sidewall spacers 26 and the spacers or caps 18 form an enclosure about top positions of the fins 16. The enclosure is formed down to the filler material 22. The materials of sidewall spacers 26 and the spacers or caps 18 include a material that is non-permeable to the agents (e.g., oxygen) capable of permeating the filler material 22.

Figure 4:
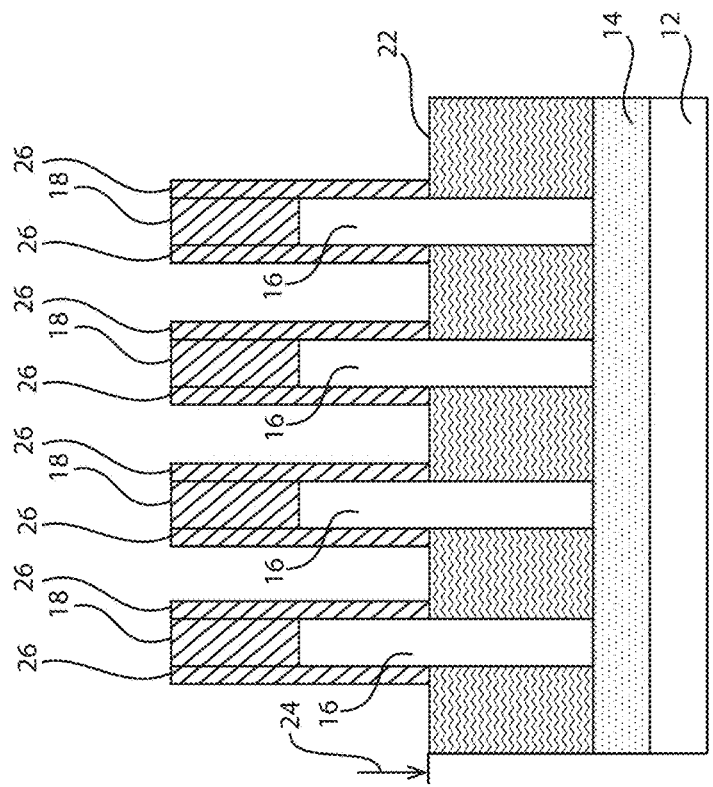
FIG. 4 is a cross-sectional view of the device of FIG. 3 showing portions of the fins within a permeable material oxidized or decomposed within the filler material to form self-aligned bird beak nodes in accordance with the present principles.

Referring to FIG. 4, as mentioned, the filler material 22 is permeable to an agent (e.g., an oxidizing agent, such as oxygen) and the spacers 18 and sidewall spacers 26 are not. In this way, when the device 10 is exposed to an oxidation process, e.g., exposed to reactive oxygen, the fins 16 within the filler material 22 decompose from crystalline semiconductor material to dielectric material. In one embodiment, the filler material 22 includes silicon oxide and the fins 16 are oxidized to also form a silicon oxide. In one embodiment, the filler material 22 is permeable to oxygen while the nitride of spacers 18 and 26 are not permeable to oxygen. Fin bottoms 28 form sharp points due to the bird's beak effect during oxidation. Similarly, fins portions 30 in contact with the doping layer 14 form corresponding sharp points due to the bird's beak effect during oxidation. The fin bottoms 28 and fin portions 30 are aligned to one another since these features are each part of a same fin 16.

Figure 5:
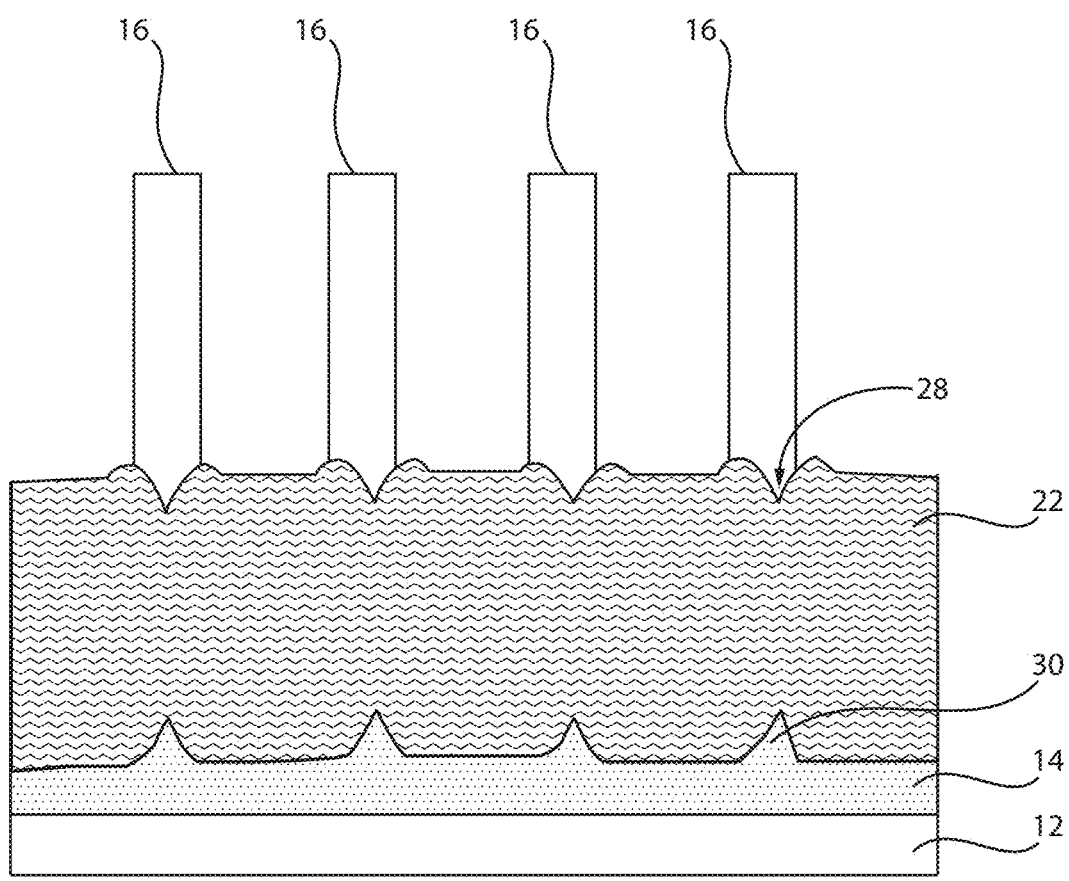
FIG. 5 is a cross-sectional view of the device of FIG. 4 showing the non-permeable material enclosing the portions of the fins removed in accordance with the present principles.

Referring to FIG. 5, the spacers 18 and 26 are removed by an etching process that selectively removes the spacers 18, 26 with respect to the filler material 22 and the fins 16. The etching process may include a dry etching process configured to selectively remove, e.g., silicon nitride, with respect to silicon oxide and silicon. The fins 16 are now exposed for additional processing.

Figure 6:
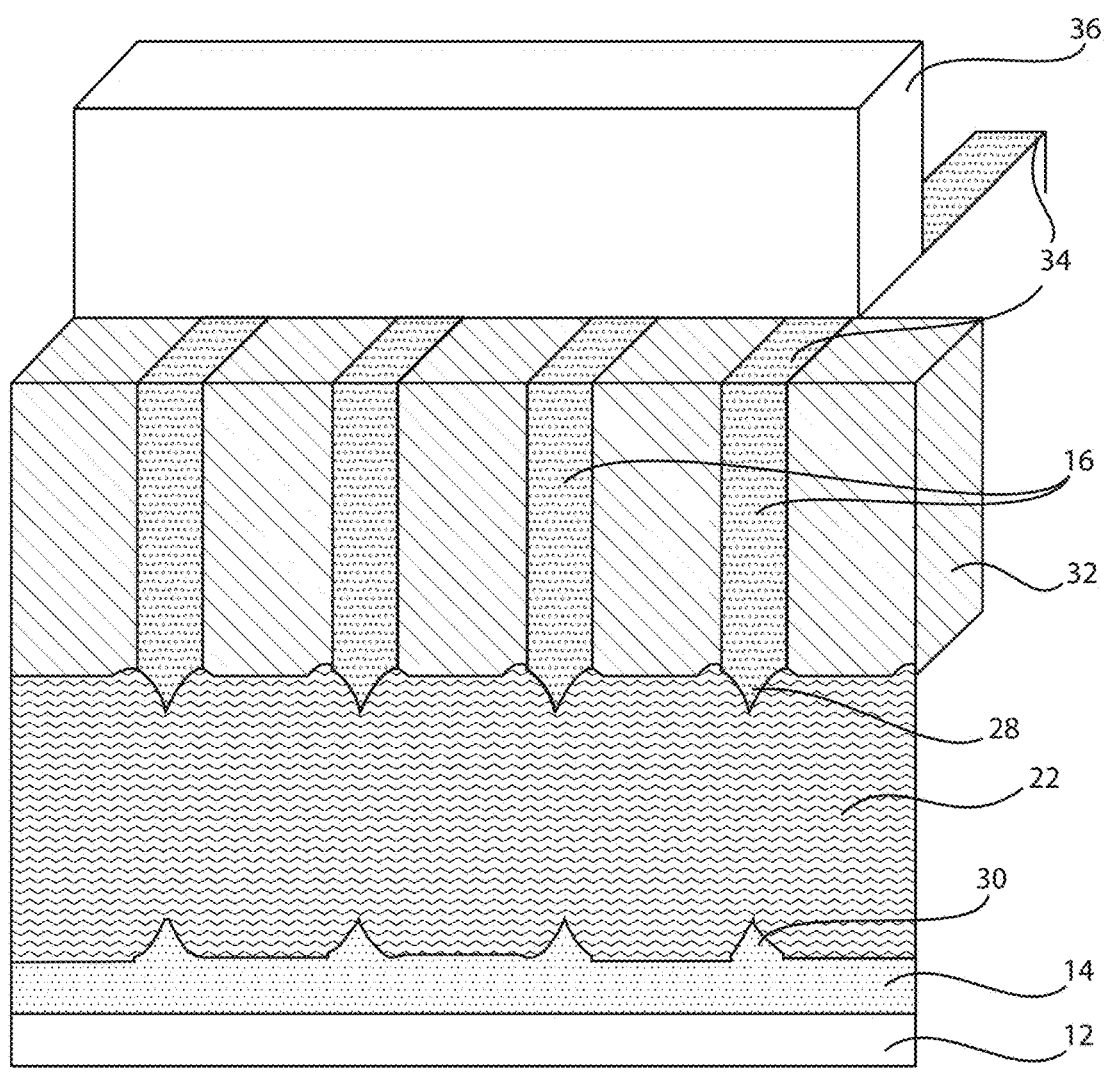
FIG. 6 is a cross-sectional view of the device of FIG. 5 showing dielectric material filling gaps between fins, a dummy gate formed and the fins doped to form source and drain regions in accordance with the present principles.

Referring to FIG. 6, another filler material 32 is formed between fins 16. The filler material 32 includes a dielectric material. In one embodiment, the filler material 32 may include a nitride material, e.g., silicon nitride. A dummy gate 36 is formed over the fins 16, and the filler material 32 acts as a doping mask for subsequent doping and activation of source and drain regions 34 formed in the fins 16. Once the dummy gate 36 is formed and patterned, the source and drain regions 34 are formed by a doping process, e.g., an implantation doping process, although other doping processes may be employed (e.g., diffusion doping, etc.).

Figure 7:
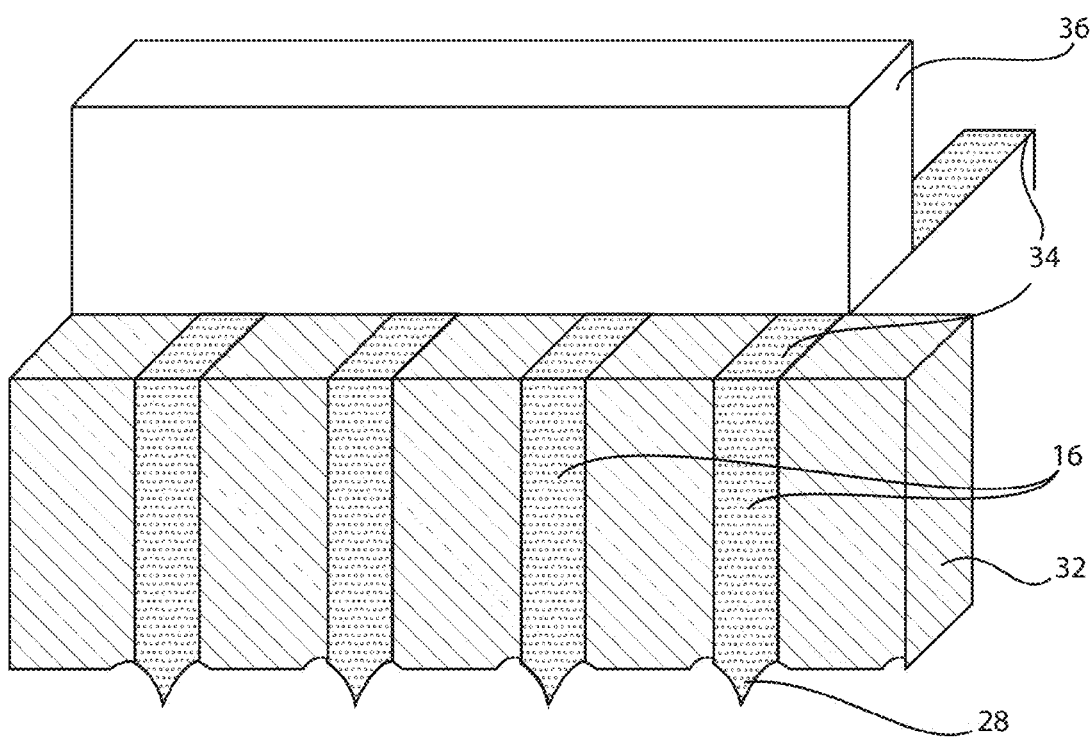
FIG. 7 is a cross-sectional view of the device of FIG. 6 showing a channel formed in accordance with the present principles.
Figure 7:
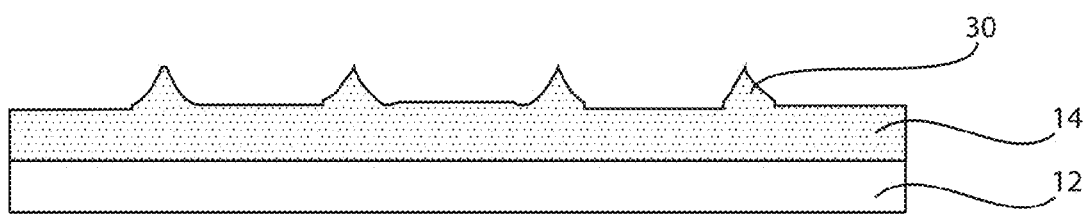

Referring to FIG. 7, the filler material 22 is removed to form a fluidic channel 40. The filler material 22 may be removed by a selective wet etch or other etching process. The source and drain regions 34 and the dummy gate 36 are supported by structures surrounding the channel 40 (e.g., the back or front of the channel 40). For example, support may be provided by filler material 32 that extends to the front and back of the source and drain regions 34.

Figure 8:
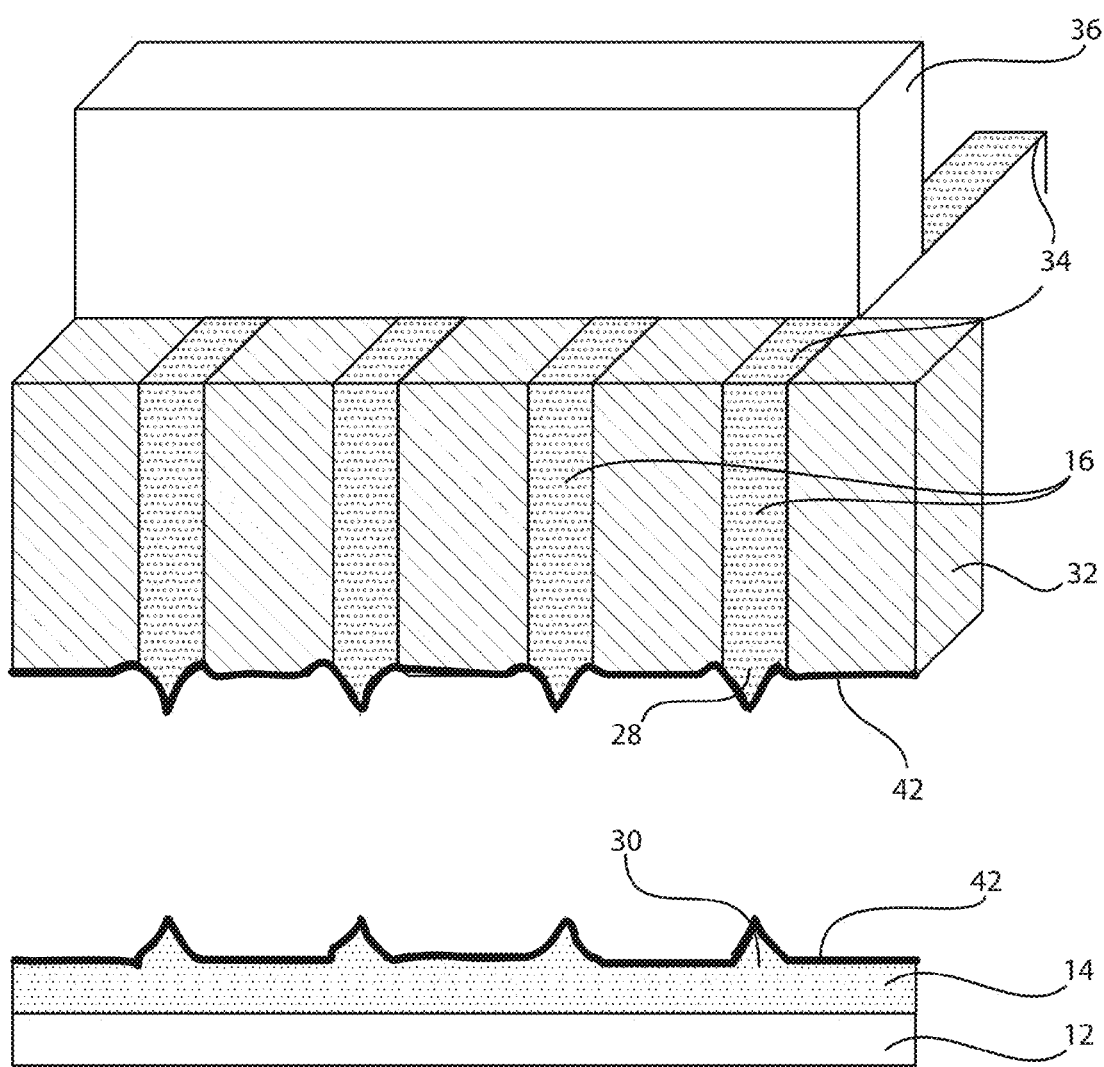
FIG. 8 is a cross-sectional view of the device of FIG. 7 showing the channel lined with a dielectric material in accordance with the present principles.

Referring to FIG. 8, the channel 40 is exposed to a gate dielectric deposition process to form a gate dielectric 42 over the filler material 32, fins 16, and the doping layer 42. The gate dielectric 42 preferably includes a high dielectric constant (high-k) dielectric material, e.g., $SiO_2$, $HfO_2$, etc.

Figure 9:
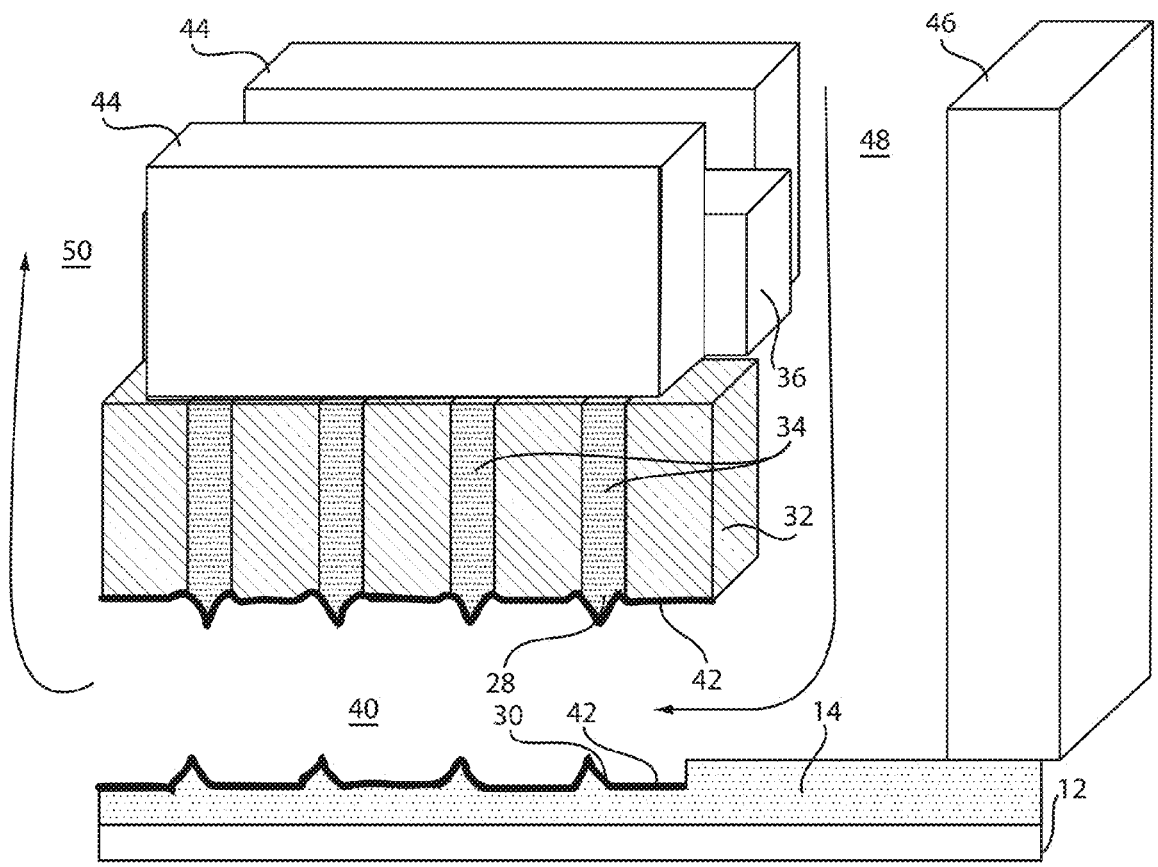
FIG. 9 is a cross-sectional view of the device of FIG. 8 showing contacts formed to the source and drain regions and to a buried doping layer to form a gate in accordance with the present principles.

Referring to FIG. 9, contacts 44 are deposited and patterned to connect source and drain regions 34 on respective sides of the dummy gate 36. A contact 46 is also formed to connect metallizations (note shown) to the doping layer 14 to provide activation voltages to the gate, which includes the buried doping layer 14. The contact 46 and other structures are employed to form trenches 48, 50 to provide access to and from the channel 40. The contacts 44, 46 may be formed from any suitable conductive material, such as a metal (e.g., Al, W, Cu, Ag, Au, etc.) and/or a metallic compound liner (e.g., TiN, TaN, etc.). The contacts 44, 46 may be coated in dielectric (not shown) to electrically isolate the contact structures. Additional metallization and circuitry may be formed on or in the structure to provide for chip functions, such as multiplexing, power, amplification, sensing functions, measurements, etc.

It should be understood that while the present principles show and describe transistor structures for sensing, detecting, moving, filtering, etc. particles in the channel 40, other electrical components or devices may be formed instead of or in addition to these elements. For example, diodes, capacitors, inductors, etc. may be formed instead of or in additional to the transistor structures depicted.

Figure 10:
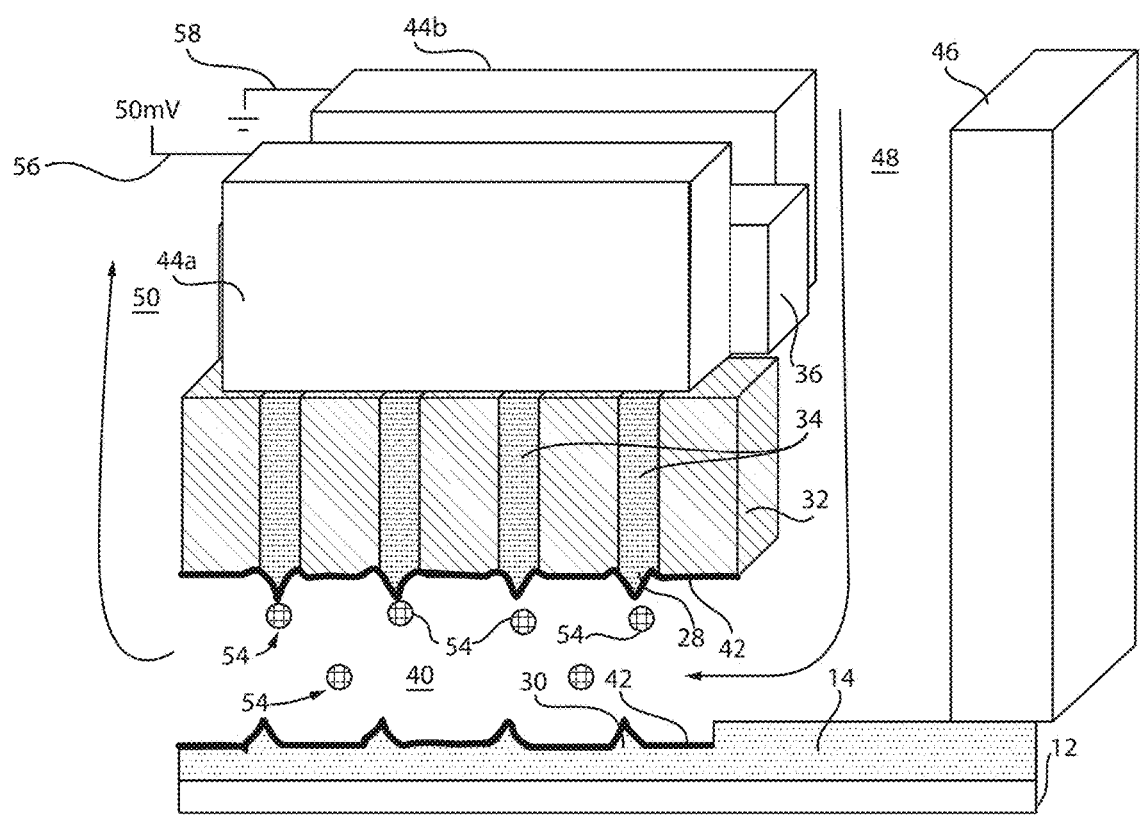
FIG. 10 is a cross-sectional view of the device of FIG. 9 showing particles flowing through trenches to and from the channel to create fluctuations in the source and drain characteristics of a transistor/detection circuit in accordance with the present principles.

Referring to FIG. 10, an illustrative example is depicted showing a possible embodiment and its operation. In this example, a source contact 44a is connected to ground 58 and a drain contact is biased at a voltage 56. The voltage 56 may be, e.g., about 50 mV, although other voltages and arrangements are contemplated. When particles (charged) 54 are passed through the channel 40, the particles 54 electrically interact with the high-k gate dielectric 42. The particle movement along the pointed electrodes 28, 30 modulates the gate potential and thus source/drain (S/D) current. The buried doping layer 14 may be considered the gate in this embodiment and provides an activating voltage to generate current across the source and drain regions 34. The buried doping layer 14 can be used at the back gate to push or pull particles using the contact 46 to alter the voltage on the buried doping layer 14.

It should be understood that the present principles provide a detection circuit; however, the circuit may be configured for sensing, moving, filtering, etc. or otherwise manipulating or identifying characteristics of particles 54 in the channel 40. Other electrical components or devices may be provided to customize the structure for such applications.

Figure 11:
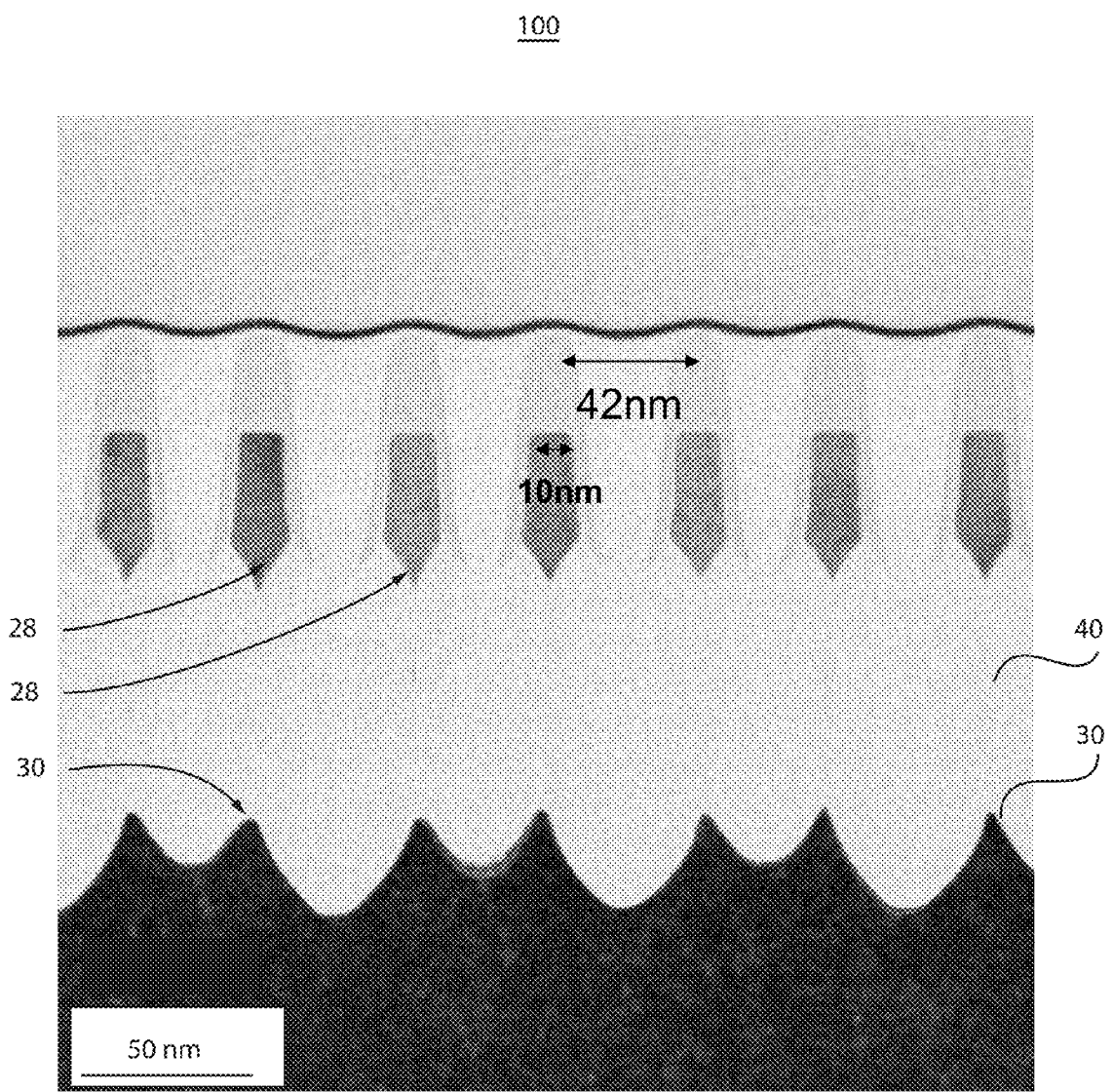
FIG. 11 is an image of a cross-section of a sensor in accordance with one illustrative embodiment.

Referring to FIG. 11, an image of a high density sensor 100 (nano-array) is shown in accordance with one embodiment. The sensor 100 includes top nodes 28 formed from semiconductor fins, e.g., Si, SiGe, etc. The top nodes 28 in this example have a width of about 10 nm and have a pitch of about 42 nm. Finer pitches and coarser pitches are also contemplated. Self-aligned bottom nodes 30 are formed in a buried doped layer on a semiconductor substrate (e.g., Si, SiGe, etc.) and disposed across a channel 40 from corresponding top nodes 28. The top nodes 28 and the bottom nodes 30 are preferably formed from a same semiconductor monolith.

Figure 12:
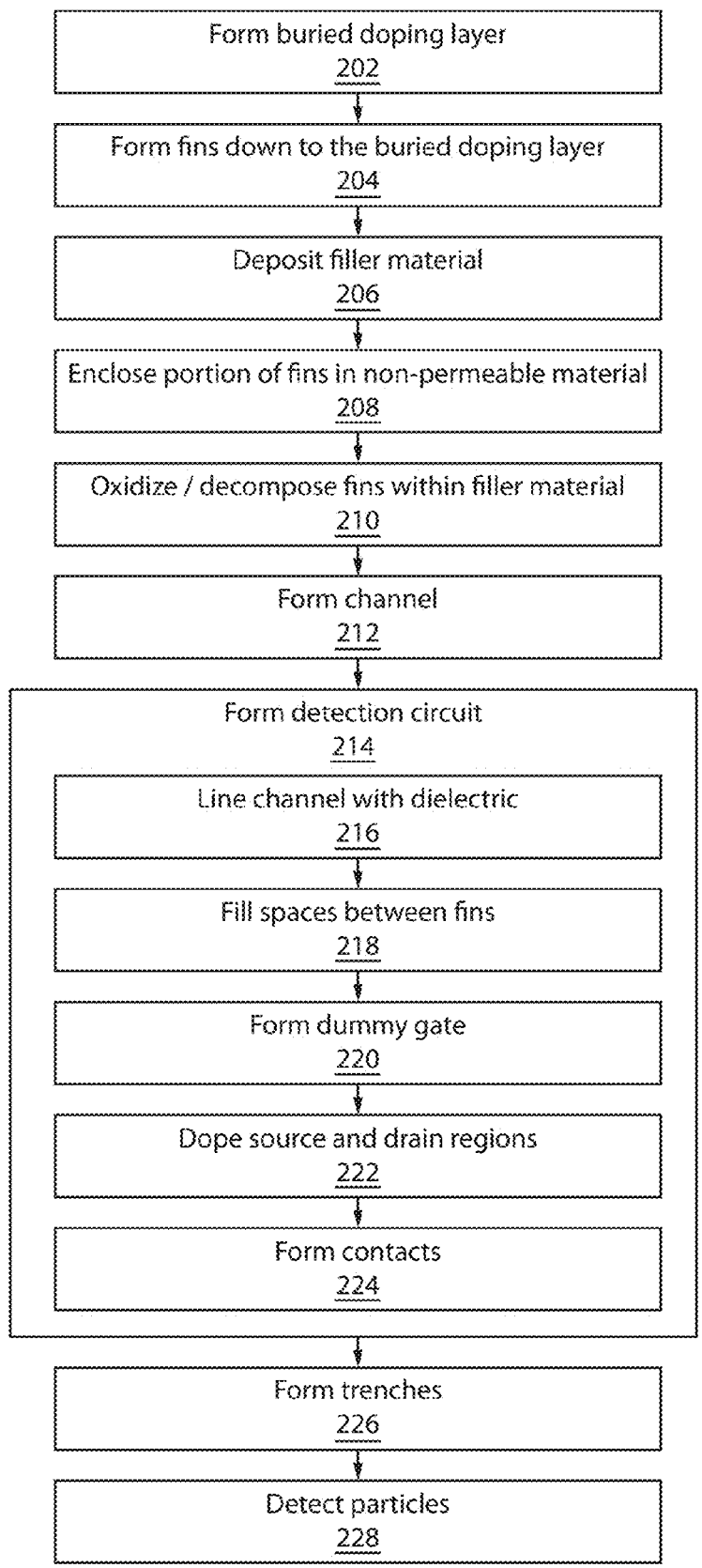
FIG. 12 is a block/flow diagram showing a method for fabricating a sensor in accordance with the present principles.

Referring to FIG. 12, a method for forming a sensor is illustratively shown. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block, 202, a buried doping layer is formed in a semiconductor substrate. The semiconductor substrate may include Si, SiGe, or other semiconductor material. The buried doping layer may be grown (epitaxy) or implanted (e.g., ion implantation). The doping levels may be controlled to control the threshold voltage of the transistors formed. The substrate includes a portion over the buried layer for forming fins. In block 204, fins are formed in the substrate down (or from) to the buried doping layer. The fins are etched from the portions of the substrate. The fins may be formed using a SIT process. In block 206, a permeable filler material is deposited from the buried doping layer to a height along the fins. The permeable filler material may include a silicon oxide and be permeable to oxygen, such that the oxygen oxidizes the semiconductor material of the fins to form a dielectric oxide.

In block 208, portions of the fin above the height are enclosed in a non-permeable material. The non-permeable material may include nitride. The non-permeable material may include a cap and spacers to enclose the fin to prevent the upper portion from oxidizing or decomposing. In block 210, the fins within the filler material are decomposed or oxidized by permeating a reactant (e.g., oxygen) through the filler material to form first pointed nodes in the portions of the fins and second pointed nodes in the buried doping layer. The first and second pointed nodes are self-aligned to each other since they are formed using a same fin. The pointed nodes are formed as points due to bird's beak effects when oxidizing or decomposing the fins within the filler material. In block 212, the filler material is removed to form a channel for receiving materials to be sensed. The first and second pointed nodes are now directed toward each other across the channel.

In block 214, components for a detection circuit (or other circuit), which couples or connects to the first and second pointed nodes, are formed. In block 216, the channel may be lined with a dielectric material (gate dielectric). The dielectric material preferably includes a high-k material. In block 218, spaces between the fins are filled with a dielectric, e.g., nitride. In block 220, a dummy gate may be formed on the portions of the fins. In block 222, the portions of the fins are doped to form source and drain regions on opposite sides of the dummy gate. The doping process may include dopant implantation, dopant diffusion, etc. In block 224, contacts are formed to the source and drain regions on opposite sides of the dummy gate, and a contact is formed down to the buried doping layer to form a gate contact.

In block 226, trenches are formed through upper layers of the device to provide access to the channel. In block 228, detecting particles in the channel is performed by measuring electrical fluctuations in the detection circuit. The particles in the channel may be suspended in a fluid such as air or water. The particles may include inorganic particles or organic particles. In organic particles may include isotopes, ions, radioactive particles, etc. Organic particles may include DNA, RNA, proteins, viruses, cells, etc. The buried doping layer, the fluid in the channel and the particles in the channel influence the gate voltage and therefore the current through the source and drain regions. Other useful configurations are also contemplated.

Having described preferred embodiments of a high density nano-array for sensing (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A sensor, comprising:
a semiconductor substrate having a buried doped layer at the surface of the substrate;
a channel having a first side adjacent to the buried doped layer and a second side opposite the first side;
first pointed nodes formed in the buried doped layer, where the first pointed nodes extend from the buried doped layer into the channel from the first side of the channel;
second pointed nodes extending into the channel from the second side of the channel, where the second pointed nodes are self-aligned with the first pointed nodes in the buried doped layer; and
the first pointed nodes and the second pointed nodes being connected to a circuit to detect particles in the channel.

2. The sensor as recited in claim 1, wherein the buried doped layer forms a gate for the circuit to detect particles.

3. The sensor as recited in claim 1, wherein the second pointed nodes are connected to source and drain regions of the circuit to detect particles.

4. The sensor as recited in claim 1, wherein the channel communicates with at least one trench to provide a flow of particles in the channel.

5. The sensor as recited in claim 1, wherein the first and second pointed nodes are formed from a same semiconductor monolith.

6. The sensor as recited in claim 1, wherein the first and second pointed nodes have a pitch of less than about 42 nm.

7. The sensor as recited in claim 1, wherein the first and second pointed nodes are covered with a dielectric layer.

* * * * *